US 7,795,195 B2

(12) United States Patent
Tanaka et al.

(10) Patent No.: US 7,795,195 B2
(45) Date of Patent: Sep. 14, 2010

(54) GEL COSMETIC COMPOSITION COMPRISING DISINTEGRABLE PARTICLES, A POLYOL, A THICKENING POLYMER AND WATER

(75) Inventors: Noriyuki Tanaka, Sumida-ku (JP); Keiko Matsuo, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/373,053

(22) PCT Filed: Aug. 24, 2007

(86) PCT No.: PCT/JP2007/000902

§ 371 (c)(1),
(2), (4) Date: Jan. 9, 2009

(87) PCT Pub. No.: WO2008/029500

PCT Pub. Date: Mar. 13, 2008

(65) Prior Publication Data

US 2009/0186792 A1 Jul. 23, 2009

(30) Foreign Application Priority Data

Aug. 29, 2006 (JP) .............................. 2006-232818

(51) Int. Cl.
*C11D 3/37* (2006.01)
*C11D 7/22* (2006.01)
*A61K 8/34* (2006.01)
*A61Q 19/10* (2006.01)

(52) U.S. Cl. .................. 510/130; 510/137; 510/145; 510/155; 510/158; 510/403; 510/475; 510/505; 424/70.11; 424/70.22; 424/70.31

(58) Field of Classification Search ................. 510/130, 510/137, 145, 155, 158, 403, 475, 505; 424/70.11, 424/70.22, 70.31
See application file for complete search history.

(56) References Cited

FOREIGN PATENT DOCUMENTS

| JP | 2000-63899 | | 2/2000 |
|---|---|---|---|
| JP | 2003 261436 | | 9/2003 |
| JP | 2003-261436 | * | 9/2003 |
| JP | 2004 43307 | | 2/2004 |
| JP | 2004-339110 | | 12/2004 |
| JP | 2006-137731 | | 6/2006 |
| JP | 2006 282659 | | 10/2006 |
| JP | 2007 261947 | | 10/2007 |

* cited by examiner

*Primary Examiner*—Brian P Mruk
(74) *Attorney, Agent, or Firm*—Oblon, Spivak, McClelland, Maier & Neustadt, L.L.P.

(57) ABSTRACT

There is provided a cosmetic composition, which stably includes disintegrable particles and is excellent in feeling upon use. A gel cosmetic composition, which has a pH of 4 to 9 and includes the following components (A), (B), (C), (D), and (E):

(A) disintegrable particles obtainable binding water-insoluble primary particles by use of a water-soluble binder;

(B) 15% to 70% by weight of polyol;

(C) a thickening polymer compound having a carboxy group;

(D) less than 1% by weight of water-soluble salts; and (E) water.

9 Claims, No Drawings

GEL COSMETIC COMPOSITION COMPRISING DISINTEGRABLE PARTICLES, A POLYOL, A THICKENING POLYMER AND WATER

FIELD OF THE INVENTION

The present invention relates to a gel cosmetic composition, which stably contains disintegrable particles and is excellent in feeling upon use.

BACKGROUND OF THE INVENTION

A cleansing composition containing particles (scrub agents) is useful for eliminating decayed corneum or removing dirt from pores. In addition, a comfortable massage feeling can also be obtained by the moderate physical stimulation attributed to the particles.

As an instance of such cleansing compositions, there are compositions containing both disintegrable particles formed by the agglomeration of primary particles, at least a part of which is water-insoluble, which are disintegrated as a result of a decrease in the concentration of water-soluble salts in an aqueous solution that contains such water-soluble salts (Patent document 1). However, since such a cleansing composition contains water-soluble salts in order to prevent disintegration of disintegrable particles in the composition, it has been difficult to thicken the system using a polymer thickener.

Polyol is generally used as a humectant in cosmetic compositions. In addition, in order to achieve special effects, for example, for the purpose of improving the permeability of an active ingredient (Patent document 2) or stably maintaining a coating state after massage for a long period of time (Patent document 3), a large amount of polyol is sometimes mixed into cosmetic compositions.

However, if a large amount of polyol is mixed into a cosmetic composition, the cosmetic composition could cause a heavy feeling upon its administration and a poor massage feeling, and also could make it difficult to treat itself due to spinnability. Moreover, since the cosmetic composition becomes sticky after being rinsed, the amount of polyol mixed is generally between a few percent and 10 percent by weight.

Patent document 1: JP-A-2000-63899
Patent document 2: JP-A-2004-339110
Patent document 3: JP-A-2006-137731

SUMMARY OF THE INVENTION

The present invention provides a cosmetic composition, which stably contains disintegrable particles and is excellent in feeling upon use.

The present inventors have found that when a large amount of polyol is used, disintegrable particles are stably contained in a cosmetic composition, and that the physical properties of the solution, such as spinnability, are improved by a thickening polymer compound having a carboxy group, so that the cosmetic composition can be easily thickened, thereby obtaining a gel cosmetic composition that provides an excellent feeling upon use.

The present invention provides a gel cosmetic composition, which has a pH of 4 to 9 and contains the following components (A), (B), (C), (D), and (E):
(A) disintegrable particles obtained as a result of the binding of water-insoluble primary particles by the action of a water-soluble binder;
(B) 15% to 70% by weight of polyol;
(C) a thickening polymer compound having a carboxy group;
(D) less than 1% by weight of water-soluble salts; and
(E) water.

With the use of a thickening polymer compound having a carboxy group, the physical properties of the solution, such as spinnability, are improved, and the cosmetic composition of the present invention is thereby thickened. In addition, the above cosmetic composition stably contains disintegrable particles without being disintegrated, and is also excellent in terms of usability. Moreover, such disintegrable particles are disintegrated in the cleaning and rinsing processes, and as a result, damage to skin or generation of itching hardly occurs. Such disintegrable particles are easily disintegrated due to rinsing water or tears, thereby providing superior rinsing performance.

DETAILED DESCRIPTION OF THE INVENTION

The disintegrable particles used as component A in the present invention may be particles formed by agglomeration of either water-insoluble primary particles only, or water-insoluble primary particles and water-soluble primary particles. Such disintegrable particles are preferably formed by agglutinating water-insoluble primary particles only, or by agglutinating water-insoluble primary particles and water-soluble primary particles by the action of a water-soluble binder. Such primary particles may be either organic particles or inorganic particles. The term "water-insoluble" is used herein to mean a solubility of less than 50% by weight obtained when 1 part by weight of target particles is dissolved in 99 parts by weight of water at 25° C., whereas the term "water-soluble" is used herein to mean a solubility of 50% or more by weight obtained under the same above conditions. It is to be noted that such solubility is measured by filtrating an aqueous solution with a filter (No. 2) and then calculating on the basis of the solid content in the filtrate. Water-soluble primary particles preferably have a solubility of 90% or more by weight.

Examples of water-insoluble organic primary particles include polyethylene, polypropylene, polyamide, polyethylene terephthalate, polystyrene, polyurethane, their cross-linked forms, sodium poly(meth)acrylate, a poly(meth)acrylic acid ester, and their cross-linked forms. Examples of such water-insoluble organic primary particles further include: synthetic polymers including rubbers such as ethylene rubber, propylene rubber, styrene-butadiene rubber, butadiene rubber or silicone rubber, and their cross-linked forms; and natural polymers such as cellulose and its derivative, chitosan and its derivative, corn starch, starch, or fruit shell, and their derivatives. Of these, polyethylene, polyamide, polystyrene, sodium poly(meth)acrylate, a poly(meth)acrylic acid ester, cellulose and its derivative, corn starch, starch, and the like are preferably used. In particular, corn starch, cellulose, and its derivative are preferably used. The term "poly(meth)acrylic acid" is herein used to mean both "polyacrylic acid" and "polymethacrylic acid."

Examples of water-insoluble inorganic primary particles include bentonite, talc, mica, kaolin, sepiolite, silica, calcium carbonate, titanium oxide, silicic acid anhydride, calcium hydroxyapatite, and pearl essence. Of these, bentonite, talc, mica, kaolin, silica, and the like are preferably used.

The form of such water-insoluble primary particle is not particularly limited. The form of such water-insoluble primary particle may be a spherical form, a substantially spherical form, or a deformed shape obtainable by crushing. In addition, hollow or porous particles, etc. can also be used.

Moreover, such water-insoluble primary particles may be used in a single type or as a mixture of two or more types.

Examples of water-soluble organic primary particles include: synthetic polymers such as polyvinyl alcohol and its derivative, poly(meth)acrylic acid alkali salts, alkali salts of a (meth)acrylic acid/(meth)acrylic acid ester copolymer, alkali salts of an acrylic acid/maleic acid copolymer, or polyvinylpyrrolidone; sugars such as methylcellulose, ethylcellulose, carboxymethylcellulose sodium, hydroxyalkylcellulose, modified starch (hydroxyalkyl-modified starch, phosphoric acid ester-modified starch, etc.), sucrose, or lactose; and natural polymers such as seaweed or a protein.

Moreover, examples of water-soluble inorganic primary particles include: chlorides such as sodium chloride, potassium chloride, or magnesium chloride; sulfates such as sodium sulfate, potassium sulfate, magnesium sulfate, or aluminum sulfate; and carbonates such as sodium carbonate or sodium bicarbonate. In the case of sodium chloride, commercially available common salts, highly purified salts, native salts, or the like can be used. Of these, inorganic particles such as sodium chloride, potassium chloride, magnesium chloride, or sodium carbonate are preferable.

The form of such a water-soluble primary particle is not particularly limited. Such water-soluble primary particles may be used in a single type or as a mixture of two or more types.

In disintegrable particles, the weight ratio between water-insoluble primary particles and water-soluble primary particles is preferably as follows: (water-insoluble primary particles)/(water-soluble primary particles)=1/99 to 100/0.

The mean particle size of such a primary particle is preferably between 1 and 70 μm. In terms of easy granulation, it is preferably between 5 and 70 μm. The mean particle size of a primary particle that is within the aforementioned range is preferable in that an uncomfortable feeling is not caused by primary particles or in terms of rinsing properties, in the process of washing an object to be washed or in a case where disintegrable particles are disintegrated with rinsing water or tears.

The mean particle size of a disintegrable particle is preferably between 70 and 800 μm, more preferably between 70 and 600 μm, and even more preferably between 70 and 360 μm. When the mean particle size of a disintegrable particle is within a range between 70 and 800 μm, the level of uncomfortable feeling or irritation to skin is particularly low at the time of use. Thus, it is preferable.

Disintegrable particles are preferably formed by agglutinating the aforementioned primary particles by the action of a water-soluble binder. It is preferable that such a water-soluble binder be dissolved in a polyol aqueous solution as a result of a decrease in the concentration of such polyol, and that it be precipitated as a result of an increase in the concentration of such polyol. Examples of such a water-soluble binder include: synthetic polymers such as polyvinyl alcohol and its derivative (itaconic acid-modified polyvinyl alcohol, sulfonic acid-modified polyvinyl alcohol, maleic acid-modified polyvinyl alcohol, etc.), poly(meth)acrylic acid alkali salts, alkali salts of a (meth)acrylic acid/(meth)acrylic acid ester copolymer, alkali salts of an acrylic acid/maleic acid copolymer, or polyvinylpyrrolidone; semisynthetic polymers such as methylcellulose, ethylcellulose, carboxymethylcellulose sodium, hydroxyalkylcellulose, or a starch derivative; and natural polymers such as starch, seaweed, plant mucilage, or a protein. Of these, polyvinyl alcohol and its derivative, carboxymethylcellulose sodium, and hydroxyalkylcellulose are preferable. Further, polyvinyl alcohol and its derivative, and carboxymethylcellulose sodium are more preferable. Still further, polyvinyl alcohol and its derivative are preferable.

The materials of the aforementioned water-soluble primary particle and water-soluble binder, which are used in disintegrable particles, may be of the same type, or of different types.

In terms of degradability of particles and workability during the production process of disintegrable particles or a cosmetic composition that contains such disintegrable particles, a water-soluble binder is preferably used at a percentage of 0.5% to 30% by weight based on the mass of primary particles.

The method of producing disintegrable particles is not particularly limited. For example, such disintegrable particles can be produced by mixing primary particles with a water-soluble binder, and/or by applying a granulation method such as tumbling granulation, tumbling flow granulation, fluidized bed granulation, agitation-tumbling granulation, melt granulation, extrusion granulation or spray drying granulation, or a coating method such as spray drying, while mixing the aforementioned components. Such disintegrable particles can also be produced by the combined use of such methods.

Disintegrable particles are characterized in that their degradation ratio increases as a result of a decrease in the concentration of polyol in an aqueous solution that contains a high concentration of polyol. Accordingly, when such disintegrable particles are mixed into a cosmetic composition, such disintegrable particles are stably dispersed in the above cosmetic composition without being disintegrated. With a decrease in the concentration of polyol during the cleansing and rinsing processes, such disintegrable particles are disintegrated. Taking into consideration the mixing of such disintegrable particles into a cosmetic composition, the degradation properties of disintegrable particles are preferably designed such that at least a portion thereof is disintegrated in an aqueous solution comprising polyol with a concentration of less than 15% by weight, and preferably 10% by weight or less. In terms of rinsing performance with rinsing water or tears, such disintegrable particles are preferably designed such that 60% or more by volume of the particles is disintegrated in an aqueous solution comprising polyol with a concentration of less than 15% by weight, and preferably 10% by weight or less. Moreover, the thus disintegrated particles preferably have a mean particle size of 80 μm or less.

One or more types of disintegrable particles can be used as component (A). In terms of excellent detergent properties and feeling upon use, such disintegrable particles may be contained at a percentage of preferably 1% to 25% by weight, and more preferably 2% to 20% by weight in the total composition.

Examples of polyol used as component (B) in the present invention include: glycols such as ethylene glycol, diethylene glycol, triethylene glycol, propylene glycol, dipropylene glycol, 1,3-butylene glycol, or 1,4-butylene glycol; glycerins such as glycerin or diglycerin; and sugar alcohols such as sorbitol, mannitol, xylitol, or maltitol.

Of these, sorbitol, mannitol, xylitol, maltitol, and glycerin are preferable.

One or more types of polyols can be used as component (B). Such polyols may be contained at a percentage of 15% to 70% by weight, preferably 15% to 60% by weight, more preferably 20% to 50% by weight, and even more preferably 31% to 50% by weight in the total composition. If less than 15% by weight of polyols are used, disintegrable particles used as component (A) cannot be stably comprised in a cosmetic composition without being disintegrated.

As a thickening polymer compound having a carboxy group used as component (C) in the present invention, a compound which comprises a carboxy group in a molecule thereof and has a crosslinked structure is preferable. Examples of such a thickening polymer compound include compounds having polyacrylic acid as a main chain and having an allyl sucrose structure or a pentaerythritol structure as a crosslinking group, such as carboxyvinyl polymers (Carbopol 980 and 981 as commercially available products (both of which were manufactured by Noveon)), and acrylic acid-alkyl methacrylate (C10-30) copolymers (Pemulen TR1 and TR2, Carbopol 1342, and ETD2020 (all of which were manufactured by Noveon)).

One or more types of thickening polymer compounds used as component (C) can be used. Such thickening polymer compounds are contained at a percentage of preferably 0.005% to 5% by weight, and more preferably 0.1% to 2% by weight in the total composition. When the thickening polymer compounds are used within the aforementioned range, the gel cosmetic composition does not feel slippery and provides both a refreshing feeling and physical properties such as a moderate thickening effect and improvement of spinnability. Thus, such thickening polymer compounds are preferably used within the aforementioned range.

Water-soluble salts used as component (D) in the present invention include water-soluble inorganic salts, and water-soluble organic salts having a total carbon number of 8 or less.

Examples of water-soluble inorganic salts include: chlorides such as sodium chloride, potassium chloride, or magnesium chloride; sulfates such as sodium sulfate, potassium sulfate, magnesium sulfate, or aluminum sulfate; and carbonates such as sodium carbonate or sodium bicarbonate. In the case of sodium chloride, commercially available common salts, highly purified salts, native salts, or the like can be used. Of these, sodium chloride, potassium chloride, magnesium chloride, and sodium carbonate are more preferable.

As water-soluble organic salts, compounds having a total carbon number of 8 or less, such as citrate, succinate, maleate, fumarate, or malate, are used.

It is also possible to use such water-soluble inorganic salts in combination with water-soluble organic salts.

Water-soluble salts used as component (D) are contained at a percentage of less than 1% by weight, and preferably less than 0.9% by weight in the total composition. Thus, it is preferable for the above cosmetic composition not to contain such water-soluble salts. If the cosmetic composition comprised 1% or more by weight of water-soluble salts, it could not be sufficiently thickened even using a thickening polymer compound, and thus it would become difficult to improve spinnability and the like.

In the present invention, water used as component (E) is contained at a percentage of preferably 25% to 80% by weight, and more preferably 35% to 70% by weight in the total composition.

The cosmetic composition of the present invention may further contain an anionic surfactant.

Examples of such an anionic surfactant include: alkyl phosphates such as potassium lauryl phosphate, sodium lauryl phosphate, arginine lauryl phosphate, potassium myristyl phosphate, sodium myristyl phosphate, arginine myristyl phosphate, potassium palmityl phosphate, sodium palmityl phosphate, or arginine palmityl phosphate; polyoxyethylene (hereinafter referred to as POE) alkyl phosphates such as sodium POE oleyl ether phosphate or sodium POE stearyl ether phosphate; alkyl sulfates such as sodium lauryl sulfate or potassium lauryl sulfate; POE alkyl ether sulfates such as POE potassium lauryl sulfate, POE sodium lauryl sulfate, or POE lauryl sulfate triethanolamine; acylated amino acid salts such as sodium lauroyl sarcosine, monosodium N-lauroyl glutamate, disodium N-stearoyl glutamate, monosodium N-myristoyl-L-glutamate, N-lauroyl glycine triethanolamine, N-lauroyl-β-alanine triethanolamine, or N-stearoyl-β-alanine triethanolamine; higher fatty acid amide sulfonates such as sodium N-myristoyl-N-methyl taurine; sulfosuccinates such as sodium di-2-ethylhexylsulfosuccinate; and amide-amino acid type surfactants such as disodium cocoamphodiacetate or disodium cocoamphodipropionate. Of these, alkyl phosphate and POE alkyl ether sulfate are preferable.

One or more types of anionic surfactants can be used. In terms of detergent properties and foaming property, such anionic surfactants are contained at a percentage of preferably 1% to 50% by weight, and more preferably 5% to 40% by weight in the total composition. The cosmetic composition of the present invention contains such anionic surfactants, so that it can be applied as a cleansing composition.

In addition, the cosmetic composition of the present invention may further contain a nonionic surfactant.

Examples of such a nonionic surfactant include a POE fatty acid ester, a POE alkyl ether, a fatty acid POE alkyl ether, a POE sorbitan fatty acid ester, a POE sorbit fatty acid ester, a POE glycerin fatty acid ester, POE hydrogenated castor oil, a polyoxyethylene polyoxypropylene alkyl ether, a polyglycerin fatty acid ester, a sucrose fatty acid ester, alkyl polyglycoside, and a sorbit fatty acid ester. Of these, a POE alkyl ether, POE hydrogenated castor oil, a sucrose fatty acid ester, and alkyl polyglycoside are preferable.

One or more types of nonionic surfactants can be used. In terms of rinsing performance and cleansing performance, such nonionic surfactants are contained at a percentage of preferably 1% to 30% by weight, and more preferably 2% to 20% by weight in the total composition. The cosmetic composition of the present invention contains such nonionic surfactants, so that it can be applied as a cleansing composition or a massaging cosmetic composition.

In the present invention, with regard to the total content of anionic surfactants and/or nonionic surfactants and the content of a thickening polymer compound having a carboxy group used as component (C), component (C)/(component (C)+(anionic surfactants and/or nonionic surfactants)) is preferably 0.02 or greater, and more preferably 0.1 or greater, in terms of the improvement of spinnability. On the other hand, if the above value is 0.2 or smaller, it is also preferable in terms of usability such as disintegrating property.

In addition, the cosmetic composition of the present invention contains components other than polyol used in common cosmetic compositions, such as a moisturizer, an oil component, a skin-lightening agent, a blood circulation-promoting agent, an anti-inflammatory agent, a microbicide, an ultraviolet absorber, a feeling improver, a coloring agent, an antiseptic, an antioxidant, and a perfume, as well as the aforementioned components, unless such components impair the effects of the present invention.

The cosmetic composition of the present invention can be produced by a common method. According to such a common method, a gel cosmetic composition can be produced. The term "gel" is used in the present invention to mean a product having a viscosity of 10,000 to 1,000,000 mPa·s at 25° C. Within the aforementioned range, the cosmetic composition is not separated. When the cosmetic composition is dispensed, it hardly drops out of the hand. Further, when it is filled in a vessel such as a tube, it is easily dispensed out of the tube.

In the present invention, when the viscosity is 10,000 mPa·s or less, it is measured at 25° C. at 12 rpm using a BM viscometer (manufactured by TOKIMEC). On the other hand, when the viscosity is greater than 10,000 mPa·s, it is measured at 25° C. at 5 rpm using a B8R-type viscometer equipped with a helical stand (manufactured by TOKIMEC).

Moreover, the cosmetic composition of the present invention has a pH between pH 4 and 9. When the cosmetic composition has such a pH value, the thickening polymer compound used as component (C) exhibits its thickening effects, and the above cosmetic composition is mild to the skin. Such a pH value may be controlled by a common method using an acid or alkali aqueous solution.

It is to be noted that the term "pH" is used in the present invention to mean the pH value of an aqueous solution that contains 5% by weight of a cosmetic composition, which is measured at 25° C.

The cosmetic composition of the present invention can be applied as a gel skin cleansing composition such as a massaging cosmetic composition, a facial cleanser, or a body cleanser.

In all cases, the cosmetic composition of the present invention is applied onto skin to massage it, and it is then cleaned and/or washed off. Disintegrable particles provide sufficient massage effects. Moreover, such disintegrable particles are disintegrated in the cleaning and rinsing processes, and as a result, damage to skin or the generation of itching does not occur, thereby providing a superior rinsing performance.

EXAMPLES

Production Example 1

Production of Disintegrable Particles 42 g of powder cellulose having a mean particle size of 30 μm, 42 g of corn starch having a mean particle size of 17 μm, and 8.5 g of micromica having a mean particle size of 6 μm were added as primary particles to an LFS-GS-2J High Speed Mixer (manufactured by Fukae Powtec), followed by preliminary blending. Thereafter, while rotating the mixture, 50 g of an aqueous solution that contained 15% by weight of polyvinyl alcohol (KM-118, manufactured by Kuraray Co., Ltd.) was gradually added as a binder thereto, followed by granulation. The thus granulated product was dried at 70° C. for 24 hours, followed by sieving, so as to obtain 50 g of disintegrable particles (1) having a mean particle size of 300 μm.

Production Example 2

The disintegrable particles produced in Production example 1 were subjected to sieving, so as to obtain 20 g of disintegrable fine particles (2) having a mean particle size of 80 μm.

Production Example 3

The disintegrable particles produced in Production example 1 were subjected to sieving, so as to obtain 5 g of disintegrable fine particles (3) having a mean particle size of 600 μm.

Examples 1 to 4 and Comparative Examples 1 to 3

The facial cleansers having the compositions as shown in Table 1 were produced by a common method, and their viscosity and pH were then measured. The produced facial cleansers were evaluated in terms of particle preservation stability, spinnability, usability/massage feeling, skin itching, and rinsing performance. The results are also shown in Table 1.

(Evaluation Method)

(1) Viscosity:

With regard to the facial cleansers having a viscosity of 10,000 mPa·s or less, the viscosity was measured at 25° C. at 12 rpm using a BM viscometer (manufactured by TOKIMEC). On the other hand, with regard to the facial cleansers having a viscosity of greater than 10,000 mPa·s, the viscosity was measured at 25° C. at 5 rpm using a B8R-type viscometer equipped with a helical stand (manufactured by TOKIMEC).

(2) pH:

Each facial cleanser was diluted 20 times with ion exchange water (an aqueous solution that contained 5% by weight of each facial cleanser), and the pH of the obtained solution was measured at 25° C. using pH METER F-22 (manufactured by Horiba, Ltd.).

(3) Particle Preservation Stability:

Each facial cleanser was preserved at 25° C. for 3 days, and it was then used. A facial cleanser, whose particles had been disintegrated and thus it did not feel granulated, was evaluated as "C." In contrast, a facial cleanser, which felt granulated and could be used in massage, was evaluated as "A."

(4) Spinnability:

Ten professional panelists used each facial cleanser. After the use, they conducted a sensory evaluation in terms of non-spinnability during the use. Such non-spinnability was evaluated according to the following standard.

A: Seven to ten panelists evaluated as favorable.

B: Six or less panelists evaluated as favorable.

(5) Usability/Massage Feeling:

Ten professional panelists used each facial cleanser. After the use, they conducted a sensory evaluation in terms of massage feeling obtained during massage. Such massage feeling was evaluated according to the following standard.

A: Seven to ten panelists evaluated as favorable.

B: Six or less panelists evaluated as favorable.

C: At least one panelist had an uncomfortable feeling or irritating feeling.

(6) Skin Itching:

Ten professional panelists massaged their face with each facial cleanser for 3 minutes. Thereafter, they conducted a sensory evaluation in terms of itching felt during the massage. Such itching was evaluated according to the following standard.

A: Seven to ten panelists felt no itching at all.

B: Six or less panelists felt no itching at all.

C: At least one panelist felt itching, an uncomfortable feeling, or irritating feeling.

(7) Rinsing Performance:

Ten professional panelists used each facial cleanser. After the use, they conducted a sensory evaluation in terms of rinsing performance that was based on the presence of particles and the remnant of the cosmetic composition during the rinsing process. Such rinsing performance was evaluated according to the following standard.

A: Seven to ten panelists evaluated as favorable.

B: Six or less panelists evaluated as favorable.

C: At least one panelist felt that the particles remained.

TABLE 1

|  | Example | | | | Comparative example | | |
|---|---|---|---|---|---|---|---|
| Component (% by weight) | 1 | 2 | 3 | 4 | 1 | 2 | 3 |
| Disintegrable particles (Production example 1) | 5.0 | 5.0 | 5.0 | 5.0 |  | 5.0 | 5.0 |
| Polyethylene beads (CL-5007, manufactured by Sumitomo Seika Chemicals) |  |  |  |  | 5.0 |  |  |
| NaCl |  | 0.1 |  |  |  | 2.0 |  |
| Acrylic acid-alkyl methacrylate copolymer (Carbopol ETD2020, manufactured by Noveon) | 1.0 | 1.0 | 0.5 | 0.5 | 1.0 | 1.0 |  |
| Glycerin | 20.0 | 20.0 |  | 23.0 | 20.0 | 20.0 | 20.0 |
| Sorbit solution (70%) | 20.0 | 20.0 | 25.0 | 35.9 | 20.0 | 20.0 | 20.0 |
| Alkyl (11-15) potassium phosphate (manufactured by Kao Corp.) | 10.0 | 10.0 |  |  | 10.0 | 10.0 | 10.0 |
| (C12-15) Pareth-2 Phosphate (manufactured by Kao Corp.) |  |  | 10.0 |  |  |  |  |
| Lauryl phosphate (manufactured by Kao Corp.) |  |  | 3.0 |  |  |  |  |
| Sodium lauryl sulfate (70%) |  |  |  | 30.0 |  |  |  |
| Laurylhydroxysulfobetaine |  |  | 5.0 | 5.0 |  |  |  |
| Octoxyglycerin |  |  | 2.0 |  |  |  |  |
| Sodium hydroxide solution (48%) |  |  |  | 3.4 |  |  |  |
| Phosphate aqueous solution (75%) | 1.2 | 1.2 |  |  | 1.2 | 1.2 | 2.8 |
| Titanium oxide |  |  |  | 0.1 |  |  |  |
| Sodium benzoate |  |  | 0.3 | 0.2 |  |  |  |
| Perfume |  |  | 0.3 | 0.3 |  |  |  |
| Purified water | Balance | Balance | Balance | Balance | Balance | Balance | Balance |
| Total | 100 | 100 | 100 | 100 | 100 | 100 | 100 |
| Viscosity (mPa·s) | 83200 | 85000 | 50000 | 80000 | 48000 | 500 | 200 |
| pH (5 weight % aqueous solution) | 5.5 | 5.6 | 6.0 | 6.5 | 5.4 | 5.5 | 5.8 |
| Particle preservation stability | A | A | A | A | A | A | A |
| Spinnability | A | A | A | A | A | B | B |
| Usability-massage feeling | A | A | A | A | C | — | — |
| Skin itching | A | A | A | A | C | — | — |
| Rinsing performance | A | A | A | A | C | — | — |

Examples 5 to 7 and Comparative Examples 4 to 8

The washout gel cosmetic compositions having the formulations as shown in Table 2 were produced in the same manner as that described in Examples 1 to 4. Thereafter, their viscosity and pH were then measured. The produced washout gel cosmetic compositions were evaluated in terms of particle preservation stability, spinnability, usability/massage feeling, skin itching, and rinsing performance. The results are also shown in Table 2.

TABLE 2

|  | Example | | | Comparative example | | | | |
|---|---|---|---|---|---|---|---|---|
| Component (% by weight) | 5 | 6 | 7 | 4 | 5 | 6 | 7 | 8 |
| Disintegrable particles (Production example 1) | 5.0 | 5.0 | 5.0 |  | 5.0 |  | 5.0 | 5.0 |
| Polyethylene beads (CL-5007, manufactured by Sumitomo Seika Chemicals) |  |  |  | 5.0 |  | 5.0 |  |  |
| NaCl |  |  | 0.01 |  | 1.0 |  | 1.0 |  |
| Polyoxyethylene (60) hydrogenated castor oil (Emanon CH-60, manufactured by Kao Corp.) | 3.0 | 3.0 | 3.0 | 3.0 | 3.0 | 3.0 | 3.0 | 3.0 |
| Glycerin | 10.0 | 20.0 | 20.0 | 10.0 | 10.0 | 20.0 | 20.0 | 5.0 |
| 1,3-butylene glycol | 10.0 | 20.0 | 20.0 | 10.0 | 10.0 | 20.0 | 20.0 |  |
| Carboxyvinyl polymer (Carbopol 980, manufactured by Noveon) | 0.6 | 0.6 | 0.6 | 0.6 | 0.6 | 0.6 | 0.6 | 0.6 |
| Potassium hydroxide solution (48%) | 0.1 | 0.1 | 0.1 | 0.1 | 0.1 | 0.1 | 0.1 | 0.1 |
| Methyl paraoxybenzoate | 0.2 | 0.2 | 0.2 | 0.2 | 0.2 | 0.2 | 0.2 | 0.2 |
| Purified water | Balance | Balance | Balance | Balance | Balance | Balance | Balance | Balance |
| Total | 100 | 100 | 100 | 100 | 100 | 100 | 100 | 100 |
| Viscosity (mPa·s) | 44000 | 60000 | 55000 | 60000 | 18 | 68000 | 18 | 44000 |
| pH (5 weight % aqueous solution) | 5.6 | 5.7 | 5.7 | 5.7 | 5.7 | 4.8 | 4.7 | 5.5 |
| Particle preservation stability | A | A | A | A | A | A | A | C |
| Spinnability | A | A | A | A | B | A | B | A |
| Usability-massage feeling | A | A | A | C | — | C | — | C |
| Skin itching | A | A | A | C | — | C | — | A |
| Rinsing performance | A | A | A | C | — | C | — | B |

Example 8

A washout gel cosmetic composition having the following formulation was produced by a common method.

An aqueous solution that contained 5% by weight of the obtained gel cosmetic composition had a pH value of pH 8.5, and the viscosity was 60,000 mPa·s at 25° C.

(Component)

| | |
|---|---|
| Disintegrable particles (Production example 2) | 20 (weight %) |
| Coconut oil fatty acid sucrose ester | 10 |
| (38% active; DK ester S-L18A, manufactured by Dai-Ichi Kogyo Seiyaku, Co., Ltd.) | |
| Glycerin | 30 |
| Mannitol | 15 |
| Acrylic acid-alkyl methacrylate (C10-30) copolymer (Pemulen TR1: manufactured by Noveon) | 0.8 |
| Sodium hydroxide solution (48%) | 0.1 |
| Phenoxyethanol | 0.2 |
| Purified water | Balance |
| Total | 100 |

Example 9

A washout gel cosmetic composition having the following formulation was produced by a common method.

An aqueous solution that contained 5% by weight of the obtained gel cosmetic composition had a pH value of pH 6.5, and the viscosity was 45,000 mPa·s at 25° C.

(Component)

| | |
|---|---|
| Disintegrable particles (Production example 3) | 2 (weight %) |
| Decyl glucoside (40% active: manufactured by Kao Corp.) | 10 |
| Glycerin | 30 |
| Mannitol | 15 |
| Acrylic acid-alkyl methacrylate (C10-30) copolymer (Pemulen TR2: manufactured by Noveon) | 0.8 |
| Sodium hydroxide solution (48%) | 0.1 |
| Phenoxyethanol | 0.2 |
| Purified water | Balance |
| Total | 100 |

Both of the gel cosmetic compositions obtained in Examples 8 and 9 stably comprised disintegrable particles, and the physical properties of solutions, such as spinnability, were improved. Thus, they could be easily thickened, thereby providing excellent usability.

What is claimed is:

1. A gel cosmetic composition, which has a pH of 4 to 9, comprising:
   (A) disintegrable particles obtained by binding water-insoluble primary particles by use of a water-soluble binder;
   (B) 15% to 70% by weight of polyol;
   (C) a thickening polymer compound having a carboxy group;
   (D) less than 1% by weight of one or more water-soluble salts; and
   (E) water,
   wherein said water-soluble binder is selected from the group consisting of polyvinyl alcohol and a derivative of polyvinyl alcohol.

2. The cosmetic composition according to claim 1, which is a cleansing composition further comprising an anionic surfactant.

3. The cosmetic composition according to claim 1, which is a cleansing composition or massaging cosmetic composition further comprising a nonionic surfactant.

4. The cosmetic composition according to claim 1, wherein (A) is present in the composition in an amount of from 1 to 25 percent by weight.

5. The cosmetic composition according to claim 1, wherein (C) is present in the composition in an amount of from 0.005 to 5 percent by weight.

6. The cosmetic composition according to claim 1, wherein (E) is present in the composition in an amount of from 25 to 80 percent by weight.

7. The cosmetic composition according to claim 1, wherein the disintegrable particles of (A) have a mean particle size of 70 to 800 μm.

8. The cosmetic composition according to claim 1, wherein the water-insoluble primary particles of (A) have a mean particle size of 1 to 70 μm.

9. The cosmetic composition according to claim 1, wherein the one or more water-soluble salts are at least one selected from the group consisting of sodium chloride, potassium chloride, magnesium chloride, sodium sulfate, potassium sulfate, magnesium sulfate, aluminum sulfate, sodium carbonate, sodium bicarbonate, citrate, succinate, maleate, fumarate, and malate.

* * * * *